(12) United States Patent
Zhu et al.

(10) Patent No.: US 6,440,991 B1
(45) Date of Patent: Aug. 27, 2002

(54) ETHERS OF 7-DESMETHLRAPAMYCIN

(75) Inventors: Tianmin Zhu, Monroe; Robin Enever, New City, both of NY (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 09/956,322

(22) Filed: Sep. 19, 2001

Related U.S. Application Data

(60) Provisional application No. 60/237,469, filed on Oct. 2, 2000.

(51) Int. Cl.[7] ..................... C07D 491/16; A61K 31/436
(52) U.S. Cl. ......................................... 514/291; 540/456
(58) Field of Search ........................... 540/456; 514/291

(56) References Cited

U.S. PATENT DOCUMENTS

| | | | |
|---|---|---|---|
| 3,929,992 A | 12/1975 | Sehgal et al. | 424/122 |
| 3,993,749 A | 11/1976 | Sehgal et al. | 424/122 |
| 4,316,885 A | 2/1982 | Rakhit | 424/122 |
| 4,401,653 A | 8/1983 | Eng | 424/114 |
| 4,650,803 A | 3/1987 | Stella et al. | 514/291 |
| 4,885,171 A | 12/1989 | Surendra et al. | 424/122 |
| 5,078,999 A | 1/1992 | Warner et al. | 424/122 |
| 5,080,899 A | 1/1992 | Sturm et al. | 514/291 |
| 5,100,883 A | 3/1992 | Schiehser | 514/291 |
| 5,100,899 A | 3/1992 | Calne | 514/183 |
| 5,118,677 A | 6/1992 | Caufield | 514/183 |
| 5,118,678 A | 6/1992 | Kao et al. | 540/452 |
| 5,120,842 A | 6/1992 | Failli et al. | 514/321 |
| 5,130,307 A | 7/1992 | Failli et al. | 514/63 |
| 5,151,413 A | 9/1992 | Caufield et al. | 514/291 |
| 5,162,333 A | 11/1992 | Failli et al. | 540/456 |
| 5,177,203 A | 1/1993 | Failli et al. | 424/122 |
| 5,206,018 A | 4/1993 | Sehgal et al. | 514/183 |
| 5,221,670 A | 6/1993 | Caufield | 540/455 |
| 5,233,036 A | 8/1993 | Hughes | 514/291 |
| 5,258,389 A | 11/1993 | Goulet et al. | 514/291 |
| 5,260,300 A | 11/1993 | Hu | 514/291 |
| 5,262,423 A | 11/1993 | Kao | 514/296 |
| 5,286,730 A | 2/1994 | Caufield et al. | 514/56 |
| 5,286,731 A | 2/1994 | Caufield et al. | 514/296 |
| 5,288,711 A | 2/1994 | Mitchell et al. | 514/56 |
| 5,302,584 A | 4/1994 | Kao et al. | 514/80 |
| 5,321,009 A | 6/1994 | Baeder et al. | 514/4 |
| 5,362,718 A | 11/1994 | Skotnicki et al. | 514/63 |
| 5,385,908 A | 1/1995 | Nelson et al. | 514/291 |
| 5,385,909 A | 1/1995 | Nelson et al. | 514/291 |
| 5,385,910 A | 1/1995 | Ocain | 514/291 |
| 5,387,589 A | 2/1995 | Kulkarni | 514/291 |
| 5,389,639 A | 2/1995 | Failli et al. | 514/291 |
| 5,391,730 A | 2/1995 | Skotnicki et al. | 540/456 |
| 5,411,967 A | 5/1995 | Kao et al. | 514/291 |
| 5,434,260 A | 7/1995 | Skotnicki et al. | 514/291 |
| 5,463,048 A | 10/1995 | Skotnicki et al. | 540/456 |
| 5,480,988 A | 1/1996 | Failli et al. | 540/456 |
| 5,480,989 A | 1/1996 | Kao et al. | 540/456 |
| 5,489,680 A | 2/1996 | Failli et al. | 540/456 |
| 5,491,231 A | 2/1996 | Nelson et al. | 540/456 |
| 5,496,832 A | 3/1996 | Armstrong | 514/291 |
| 5,504,091 A | 4/1996 | Molnar-Kimber et al. | 514/291 |
| 5,516,770 A | 5/1996 | Waranis et al. | 514/183 |
| 5,516,781 A | 5/1996 | Morris et al. | 514/291 |
| 5,530,006 A | 6/1996 | Waranis et al. | 514/291 |
| 5,536,729 A | 7/1996 | Waranis et al. | 514/291 |
| 5,559,121 A | 9/1996 | Harrison | 514/291 |
| 5,561,138 A | 10/1996 | Armstrong | 514/291 |
| 5,616,588 A | 4/1997 | Waranis et al. | 514/291 |
| 5,665,772 A | 9/1997 | Cottens et al. | 514/514 |
| 5,728,710 A | 3/1998 | Luengo | 514/291 |
| 5,780,462 A | 7/1998 | Lee et al. | 514/183 |
| 5,985,325 A | 11/1999 | Nagi | 424/482 |
| 5,989,591 A | 11/1999 | Nagi | 424/493 |

OTHER PUBLICATIONS

C.V. Vezina et al., J. Anitbiot., 1975, 721, 28.
H.A. Baker et al., J. Anitbiot., 1978, 539, 31.
FASEB, 1989, 3411, 3.
FASEB, 1989, 5256, 3.
R.Y. Calne et al., Lancet, 1978, 1183.
R. Martel et al., Can. J. Physiol. Pharmacol., 1977, 48, 55.
T. Matsumoto et al., Atheroschlerosis, 1998, 95, 139.
S.E. Roselaar et al., J. Clin. Invest., 1995, 1906, 96.
K.B. Lemstrom et al., Arterioscler. Thomb. Vasc. Biol., 1996, 553, 16(4).
T. Quaschning et al., Kidney Int., 1999, S235, 56(71).
E.E. Emeson et al., Am. J. Pathol., 1993, 1906, 142(6).
S.M. Stepkowski et al., Transplantation Proc., 1991, 507, 23.

*Primary Examiner*—Bruck Kifle
(74) *Attorney, Agent, or Firm*—Arnold S. Milowsky

(57) ABSTRACT

This invention provides ethers of 7-desmethylrapamycin which are useful in inducing immunosuppression and in the treatment of transplantation rejection, autoimmune diseases, solid tumors, fungal infections, and vascular disease.

12 Claims, No Drawings

ETHERS OF 7-DESMETHLRAPAMYCIN

This application claims priority from copending provisional application Ser. No. 60/237,469, filed Oct. 2, 2000, the entire disclosure of which is hereby incorporated by reference.

BACKGROUND OF THE INVENTION

This invention relates to ethers of 7-desmethyirapamycin, which are useful in inducing immunosuppression and in the treatment of transplantation rejection, autoimmune diseases, solid tumors, fungal infections, and vascular disease or disorders.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31, 539 (1978); U.S. Pat. No. 3,929,992; and U.S. Pat. No. 3,993,749]. Additionally, rapamycin alone (U.S. Pat. No. 4,885,171) or in combination with picibanil (U.S. Pat. No. 4,401,653) has been shown to have antitumor activity.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., Lancet 1183 (1978); and U.S. Pat. No. 5,100,899]. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

Rapamycin is also useful in preventing or treating systemic lupus erythematosus [U.S. Pat. No. 5,078,999], pulmonary inflammation [U.S. Pat. No. 5,080,899], insulin dependent diabetes mellitus [U.S. Pat. No. 5,321,009], skin disorders, such as psoriasis [U.S. Pat. No. 5,286,730], bowel disorders [U.S. Pat. No. 5,286,731], smooth muscle cell proliferation and intimal thickening following vascular injury [U.S. Pat. Nos. 5,288,711 and 5,516,781], adult T-cell leukemia/lymphoma [European Patent Application 525,960 A1], ocular inflammation [U.S. Pat. No. 5,387,589], malignant carcinomas [U.S. Pat. No. 5,206,018], cardiac inflammatory disease [U.S. Pat. No. 5,496,832], and anemia [U.S. Pat. No. 5,561,138].

Ethers-of rapamycin are disclosed in U.S. Pat. No. 5,665,772. In particular, 42-O-(2-hydroxy)ethyl rapamycin, also known as SDZ-RAD, has been reported to be useful in treating or inhibiting transplant rejection.

The preparation and use of 7-desmethylrapamycin and certain derivatives thereof are disclosed in U.S. Pat. No. 5,728,710.

DESCRIPTION OF THE INVENTION

This invention provides ethers of 7-desmethylrapamycin having the structure

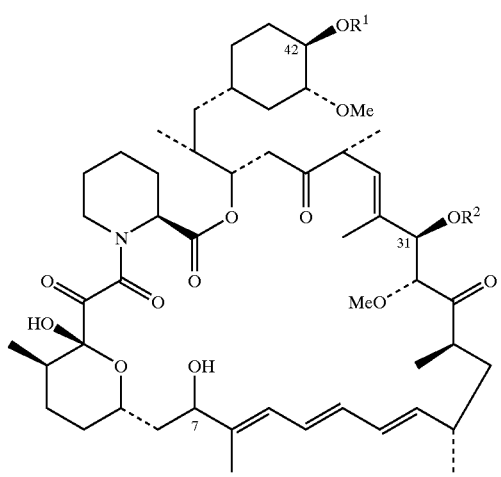

wherein $R^1$ and $R^2$ are each, independently, hydrogen, thioalkyl of 1–6 carbonlatoms, arylalkyl of 7–10 carbon atoms, hydroxyalkyl of 1–6 carbon atoms, dihydroxyalkyl of 1–6 carbon atoms, alkoxyalkyl of 2–12 carbon atoms, hydroxyalkoxyalkyl of 2–12 carbon atoms, acyloxyalkyl of 3–12 carbon atoms, aminoalkyl, of 1–6 carbon atoms, alkylaminoalkyl of 1–6 carbon atoms per alkyl group, dialkylaminoalkyl of 1–6 carbon atoms per alkyl group, alkoxycarbonylaminoalkyl of 3–12 carbon atoms, acylaminoalkyl of 3–12 carbon atoms, alkenyl of 2–7 carbon atoms, arylsulfamidoalkyl having 1–6 carbon atoms in the alkyl group, hydroxyalkylallyl of 4–9 carbon atoms, dihydroxyalkylallyl of 4–9 carbon atoms, or dioxolanylallyl;

with the proviso that $R^1$ and $R^2$ are both not hydrogen, or a pharmaceutically acceptable salt thereof which are useful for inducing immunosuppression, and in the treatment of transplantation rejection, graft vs. host disease, autoimmune diseases, diseases of inflammation, adult T-cell leukemia/lymphoma, solid tumors, fungal infections, cardiovascular disease, cerebral vascular disease, peripheral vascular disease or hyperproliferative vascular disorders.

When applicable, pharmaceutically acceptable salts can be formed from organic and inorganic bases (i.e., when a compound contains a free hydroxyl group), such as alkali metal salts (for example, sodium, lithium, or potassium) alkaline earth metal salts, ammonium salts, alkylammonium salts containing 1–6 carbon atoms or dialkylammonium salts containing 1–6 carbon atoms in each alkyl group, and trialkylammonium salts containing 1–6 carbon atoms in each alkyl group, when the rapamycin or antiestrogen contains a suitable acidic moiety.

The term alkyl includes both branched and straight chain moieties. It is preferred that aryl groups are phenyl or naphthyl. This invention covers compounds in which the stereochemistry of the 7-position is racemic (R,S) as well as the individual R and S stereoisomers at the 7-position.

As used in accordance with this invention, the term "providing," with respect to providing a compound or substance covered by this invention, means either directly administering such a compound or substance, or administering a prodrug, derivative, or analog which will form the equivalent amount of the compound or substance within the body.

Of the compounds of this invention, it is preferred that $R^2$ is hydrogen, and more prefered that $R^2$ is hydrogen and $R^1$ is hydroxyalkyl. 42-O-(2-Hydroxy)ethyl 7-desmethylrapamycin acid is particularly preferred.

The reagents used in the preparation of the compounds of this invention can be either commercially obtained or can be prepared by standard procedures described in the literature.

The preparation of the ethers of rapamycin, from which the 7-desmethylrapamycin ethers are made from, are described in U.S. Pat. No. 5,665,772, which is hereby incorporated by reference. The conversion of the 7-(S)-methoxy group of the rapamycin hydroxyester to the 7-(R,S)-hydroxy group can be accomplished by nucleophilic substitution in the mixture of water and aprotic organic solvent such as acetonitrile in acidic condition. The ratio of aqueous to organic solvent is preferred between 1:9 and 9:1, more preferred is between 1:2 and 2:1. Most preferred ratio of aqueous to organic solvent is 1:1. Resolution of the 7-isomers can be accomplished by standard methodology, such as preparative HPLC.

The antifungal activity for the ethers of 7-desmethylrapamycin of this invention was confirmed in a standard pharmacological test procedure which measured the ability of the compound being evaluated to inhibit fungal growth. 42-O-(2-Hydroxy)ethyl 7-desmethylrapamycin acid (Compound I) was evaluated as a representative compound of this invention. The procedure used and results obtained are briefly described below. A 96 U-bottom microtiter plate was filled (50 µl/well) with RPMI 1640. The compounds to be evaluated were placed in appropriate wells, and serial diluted in successive wells to provide 11 dilutions. The concentrations ranged from 64 through 0.06 µug/ml. An adjusted inoculum of fungi (50 µl) was added to each well and the plates were incubated at 35° C. for 24–48 hours. The MIC is the lowest concentration of compound which completely inhibited growth of organism in the wells. The following table shows the results obtained in this standard pharmacological test procedure. Where the same fungi is listed more than once, it indicates that more than one strain was evaluated. Nystatin and amphotericin B were used for the purpose of comparison.

TABLE 1

ANTIFUNGAL ACTIVITY (MIC in µg/mL)

| Yeast/Fungi | ID | Compound I | Nystatin | Amphotericin B |
|---|---|---|---|---|
| Candida albicans | 1063 | 1 | 1 | ≦0.06 |
| Candida albicans | 1117 | 2 | 1 | 0.12 |
| Candida albicans | ATCC 90028 | 2 | 1 | 0.12 |
| Candida parapsilosis | 94-9 | 2 | 1 | 0.12 |
| Candida parapsilosis | 94-8 | 2 | 2 | ≦0.06 |
| Candida parapsilosis | ATCC 90018 | 2 | 2 | ≦0.06 |
| Candida pseudotropicalis | ATCC 28838 | 2 | 1 | ≦0.06 |
| Candida tropicalis | 94-14 | 0.5 | 1 | ≦0.06 |
| Candida tropicalis | 94-13 | 0.5 | 1 | ≦0.06 |
| Candida krussii | 94-2 | 0.5 | 1 | 0.12 |
| Candida lusitaniae | 94-3 | 1 | 1 | ≦0.06 |
| Candida rugosa | 94-10 | 1 | 1 | 0.25 |
| Aspergillus fumigatus | ATCC 26933 | 64 | 2 | 0.25 |
| Aspergillus niger | S430 | 64 | 1 | 0.25 |
| Aspergillus niger | S399 | 64 | 2 | 0.50 |

The results obtained in this standard pharmacological test procedure demonstrate that the compounds of this invention are useful as antifungal agents.

The antineoplastic activity of the compounds of this invention were confirmed in a standard pharmacological test procedure which measures the inhibition of U87MG human glioblastoma cell growth (as a function of $^3$H-thymidine incorporation), using 42-O-(2-hydroxy)ethyl 7-desmethylrapamycin (Compound I) as a representative compound of this invention. The following briefly describes the procedure used and results obtained. U87MG human glioblastoma cells (ATCC # HTB-14; available from the American Type Culture Collection; 10801 University Boulevard; Manassas, Va. 20110;), were grown in the following media.

Growth Medium: BRL Minimum Essential Medium with Earle Salts (500 mL)

+5 mL BRL MEM Non-Essential Amino Acids (10 mM)
+5 mL BRL Penicillin-Streptomycin (1 0000u/mL,1 0000 µg/mL)
+5 mL BRL Na Pyruvate Solution (100 mM)
+5 mL BRL L-Glutamine 200 mM
+50 mL BRL Fetal Bovine Serum (Qualified)

Test Procedure:

1. Cells were trypsinized and plated at a concentration of $10^4$ cells/well in a final volume of 200 µL growth medium in 96-well flat bottom plates and allowed to adhere for 24 hours at 37° C.
2. The media was removed by aspiration with care to not disturb the cell monolayer. 200 µL of fresh growth media was added per well, allowing enough wells for samples to be run in triplicate. Test compounds were added in 10 µL phosphate buffer solution (PBS) and incubated for another 48 hours at 37° C.
3. During the last 5 hours of incubation, plates were labeled with 1 µCi $^3$H thymidine per well. (New England Nuclear thymidine, catalog #NET-027, 6.7 Ci/mmole). The 1 µCi was added in 10 µL of PBS (on the day of harvest). The plates were returned to the incubator for the last 5 hours.
4. The radioactive media was removed by aspiration, with care not to disturb the cell monolayer. Then 50 µL of BRL 1× Trypsin was added to each well, followed by incubation at 37° C. for 10 minutes or until the monolayer was loosened from the well bottom. Samples were harvested on a glass fiber filter mat using a Skatron 96 well harvester. Mats were counted in a Wallac Betaplate counter.

Results:

| Compound | $IC_{50}$ |
|---|---|
| Compound I | 3.5 ng/mL |

The results obtained in this standard pharmacological test procedure show that the compounds of this invention inhibit tumor cell growth and are therefore useful as antineoplastic agents. In particular, the compounds of this invention are useful in treating or inhibiting the growth of solid tumors, including sarcomas and carcinomas, such as astrocytomas, prostate cancer, breast cancer, small cell lung cancer, and ovarian cancer.

The compounds of this invention are also useful treatment or inhibition of transplantation rejection such as kidney, heart, liver, lung, bone marrow, pancreas (islet cells), cornea, small bowel, and skin allografts, and heart valve xenografts; in the treatment or inhibition of graft vs. host disease; in the treatment or inhibition of autoimmune diseases such as lupus, rheumatoid arthritis, diabetes mellitus, myasthenia gravis, and multiple sclerosis; and diseases of inflammation such as psoriasis, dermatitis, eczema, seborrhea, inflammatory bowel disease, pulmonary inflammation (including asthma, chronic obstructive pulmonary disease, emphysema, acute respiratory distress syndrome, bronchitis, and the like) and ocular uveitis; adult T-cell leukemiallymphoma; fungal infections; hyperproliferative vascular diseases such as restenosis; graft vascular atherosclerosis; and cardiovascular disease, cerebral vascular disease, and peripheral vascular disease, such as coronary artery disease, cerebrovascular disease, arteriosclerosis, atherosclerosis, nonatheromatous arteriosclerosis, or vascular wall damage from cellular events leading toward immune mediated vascular damage, and inhibiting stroke or multiinfarct dementia.

When used for restenosis, it is preferred that the compounds of this invention are used to treat restenosis that occurs following an angioplasty procedure. When used for this treating restenosis following an angioplasty, the compounds of this invention can be administered prior to the procedure, during the procedure, subsequent to the procedure, or any combination of the above.

It is contemplated that when the compounds of this invention are used as an immunosuppressive or antiinflammatory agent, they can be administered in conjunction with one or more other immunoregulatory agents. Such other immunoregulatory agents include, but are not limited to azathioprine, corticosteroids, such as prednisone and methylprednisolone, cyclophosphamide, rapamycin, cyclosporin A, FK-506, OKT-3, mycophenolate, and ATG. By combining the compounds of this invention with such other drugs or agents for inducing immunosuppression or treating inflammatory conditions, the lesser amounts of each of the agents are required to achieve the desired effect. The basis for such combination therapy was established by Stepkowski whose results showed that the use of a combination of rapamycin and cyclosporin A at subtherapeutic doses significantly prolonged heart allograft survival time. [Transplantation Proc. 23: 507 (1991)].

When used in the treatment or inhibition of vascular disease, it is contemplated that the compounds of this invention may be used as the sole active ingredient to provide the cardiovascular, cerebral, or peripheral vascular benefits covered by this invention, or may be administered in combination with other agents which provide beneficial cardiovascular, cerebral, or peripheral vascular effects. Such agents are generally in the classes of compounds known as ACE inhibitors, such as quinapril, perindopril, ramipril, captopril, trandolapril, fosinopril, lisinopril, moexipril, and enalapril; angiotensin II receptor antagonists, such as candesartan, irbesartan, losartan, valsartan, and telmisartan; fibric acid derivatives, such as clofibrate, and gemfibrozil; HMG Co-A reductase inhibitors, such as cerivastatin, fluvastatin, atorvastatin, lovastatin, pravastatin, simvastatin; beta adrenergic blocking agents, such as sotalol, timolol, esmolol, carteolol, propranolol, betaxolol, penbutolol, nadolol, acebutolol, atenolol, metoprolol, and bisoprolol; calcium channel blockers, such as nifedipine, verapamil, nicardipine, diltiazem, nimodipine, amlodipine, felodipine, nisoldipine, and bepridil; antioxidants; anticoagulants such as, warfarin, dalteparin, heparin, enoxaparin, and danaparoid; and agents useful in hormone replacement therapy containing estrogens, such as conjugated estrogens, ethinyl estradiol, 17-beta-estradiol, estradiol, and estropipate.

When administered for the treatment or inhibition of a particular disease state or disorder, it is understood that the effective dosage of the ether of 7-desmethylrapamycin may vary depending upon the particular compound utilized, the mode of administration, the condition, and severity thereof, of the condition being treated, as well as the various physical factors related to the individual being treated. As used in accordance with invention, satisfactory results may be obtained when the ether of 7-desmethylrapamycin is administered in a daily oral dosage of from about projected daily dosages of active compound would be 0.1 $\mu$g/kg–100 mg/kg, preferably between 0.001–25 mg/kg, and more preferably between 0.01–5 mg/kg. The projected daily dosages are expected to vary with route of administration.

Such doses may be administered in any manner useful in directing the active compounds herein to the recipient's bloodstream, including orally, via implants, parenterally (including intravenous, intraperitoneal and subcutaneous injections), rectally, intranasally, vaginally, and transdermally.

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidol silicon dioxide, phosphates, sodium dodecylsulfate, magnesium aluminum silicate, and triethanolamine. Oral formulations herein may utilize standard delay or time release formulations to alter the absorption of the active compound (s). The oral formulation may also consist of administering the active ingredient in water or a fruit juice, containing appropriate solubilizers or emulsifiers as needed.

In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into-the blood stream such as a semi-permeable membrane covering a reservoir containing the active ingredient with or without a carrier, or a matrix containing the active ingredient. Other occlusive devices are known in the literature.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

The preparation of representative examples of this invention is described below.

EXAMPLE 1

Preparation of 42-O-(2-Hydroxy)ethyl 7-desmethyirapamycin (Compound I)

42-O-(2-Hydroxy)ethyl rapamycin (30 mg, 3.13×10−5 mole) was dissolved in 20 mL acetonitrile and 20 mL 0.1 N hydrochloric acid. The solution was kept at room temperature overnight. Then the reaction mixture was extracted with 80 mL methylene chloride (CH$_2$Cl$_2$) in a separatory funnel, The organic layer was washed 100 mL water, 50 mL 0.1 M sodium phosphate buffer (pH 7) and then 100 mL water again. The methylene chloride was removed by rotary evaporation. The pure compound I was performed by preparative HPLC on a Prep Nova-pak HR C18 (300×19 mm) column from Waters. Compound I eluted at between 11.7–13.1 min and 42-O-(2-hydroxy)ethyl rapamycin eluted at 22.7 min using a gradient (0–5 min 40% A, 40% B, 5–25 min from 50% B to 70%, 25–30 min 70% B to 100% B). A is 90% water, 10% acetonitrile; B is 10% water, 90% acetonitrile. The fraction was collected and extracted by 2×100 mL methylene chloride. The organic layer was combined and dried with anhydrous sodium sulfate. Then most of the solvent was removed by rotary evaporation and final product was precipitated by hexane. Compound I, a white solid was obtained. Positive ion mass 1spectrum shows the molecular ion specie [M+NH$_4$]$^+$ at m/z 961.6. The loss of 14 from the mass of 42-O-(2-hydroxy)ethyl rapamycin indicates the conversion of a methoxy to a hydroxy. $^1$H NMR (400 MHz) of compound I in CDCl$_3$ shows the loss of 7-position CH$_3$O-resonance at 3.14 ppm comparing to the $^1$H NMR of 42-O-(2-hydroxy)ethyl rapamycin.

What is claimed is:

1. A compound having the structure

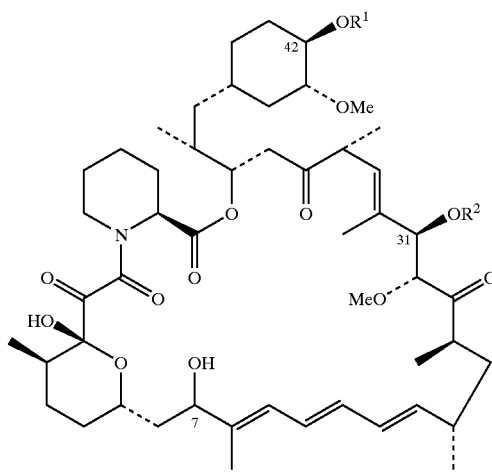

wherein

R$^1$ and R$^2$ are each, independently, hydrogen, thioalkyl of 1–6 carbon atoms, arylalkyl of 7–10 carbon atoms, hydroxyalkyl of 1–6 carbon atoms, dihydroxyalkyl of 1–6 carbon atoms, alkoxyalkyl of 2–12 carbon atoms, hydroxyalkoxyalkyl of 2–12 carbon atoms, acyloxyalkyl of 3–12 carbon atoms, aminoalkyl of 1–6 carbon atoms, alkylaminoalkyl of 1–6 carbon atoms per alkyl group, dialkylaminoalkyl of 1–6 carbon atoms per alkyl group, alkoxycarbonylaminoalkyl of 3–12 carbon atoms, acylaminoalkyl of 3–12 carbon atoms, alkenyl of 2–7 carbon atoms, arylsulfamidoalkyl having 1–6 carbon atoms in the alkyl group, hydroxyalkylallyl of 4–9 carbon atoms, dihydroxyalkylallyl of 4–9 carbon atoms, or dioxolanylallyl; with the proviso that R$^1$ and R$^2$ are both not hydrogen, or a pharmaceutically acceptable salt thereof.

2. The compound according to claim 1, wherein R$^2$ is hydrogen.

3. The compound according to claim 2, wherein R$^1$ is hydroxyalkyl of 1–6 carbon atoms.

4. The compound of claim 1, which is 42-O-(2-hydroxy)ethyl 7-desmethylrapamycin.

5. A method of treating or inhibiting transplant rejection or graft vs. host disease in a mammal in need thereof, which comprises providing to said mammal an effective amount of a compound having the structure

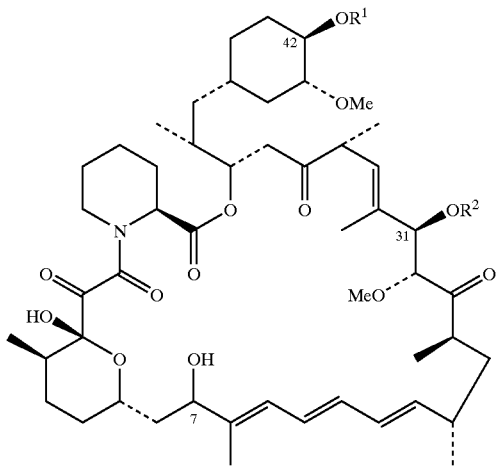

wherein

R¹ and R² are each, independently, hydrogen, thioalkyl of 1–6 carbon atoms, arylalkyl of 7–10 carbon atoms, hydroxyalkyl of 1–6 carbon atoms, dihydroxyalkyl of 1–6 carbon atoms, alkoxyalkyl of 2–12 carbon atoms, hydroxyalkoxyalkyl of 2–12 carbon atoms, acyloxyalkyl of 3–12 carbon atoms, aminoalkyl of 1–6 carbon atoms, alkylaminoalkyl of 1–6 carbon atoms per alkyl group, dialkylaminoalkyl of 1–6 carbon atoms per alkyl group, alkoxycarbonylaminoalkyl of 3–12 carbon atoms, acylaminoalkyl of 3–12 carbon atoms, alkenyl of 2–7 carbon atoms, arylsulfamidoalkyl having 1–6 carbon atoms in the alkyl group, hydroxyalkylallyl of 4–9 carbon atoms, dihydroxyalkylallyl of 4–9 carbon atoms, or dioxolanylallyl;

with the proviso that R¹ and R² are both not hydrogen, or a pharmaceutically acceptable salt thereof.

6. A method of treating or inhibiting a solid tumor selected from the group consisting of astrocytoma, prostate cancer, breast cancer, small cell lung cancer, and ovarian cancer in a mammal in need thereof, which comprises providing to said mammal a compound having the structure

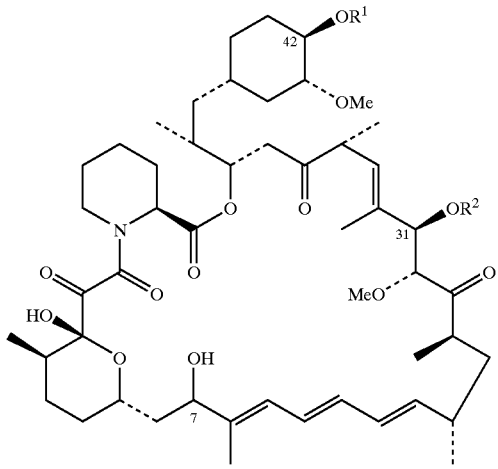

wherein

R¹ and R² are each, independently, hydrogen, thioalkyl of 1–6 carbon atoms, arylalkyl of 7–10 carbon atoms, hydroxyalkyl of 1–6 carbon atoms, dihydroxyalkyl of 1–6 carbon atoms, alkoxyalkyl of 2–12 carbon atoms, hydroxyalkoxyalkyl of 2–12 carbon atoms, acyloxyalkyl of 3–12 carbon atoms, aminoalkyl of 1–6 carbon atoms, alkylaminoalkyl of 1–6 carbon atoms per alkyl group, dialkylaminoalkyl of 1–6 carbon atoms per alkyl group, alkoxycarbonylaminoalkyl of 3–12 carbon atoms, acylaminoalkyl of 3–12 carbon atoms, alkenyl of 2–7 carbon atoms, arylsulfamidoalkyl having 1–6 carbon atoms in the alkyl group, hydroxyalkylallyl of 4–9 carbon atoms, dihydroxyalkylallyl of 4–9 carbon atoms, or dioxolanylallyl; with the proviso that R¹ and R² are both not hydrogen, or a pharmaceutically acceptable salt thereof.

7. A method of treating or inhibiting a fungal infection in a mammal in need thereof, which comprises providing to said mammal an effective amount of a compound having the structure

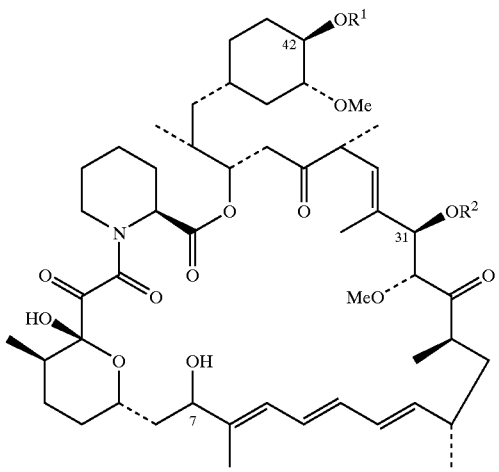

wherein

R¹ and R² are each, independently, hydrogen, thioalkyl of 1–6 carbon atoms, arylalkyl of 7–10 carbon atoms, hydroxyalkyl of 1–6 carbon atoms, dihydroxyalkyl of 1–6 carbon atoms, alkoxyalkyl of 2–12 carbon atoms, hydroxyalkoxyalkyl of 2–12 carbon atoms, acyloxyalkyl of 3–12 carbon atoms, aminoalkyl of 1–6 carbon atoms, alkylaminoalkyl of 1–6 carbon atoms per alkyl group, dialkylaminoalkyl of 1–6 carbon atoms per alkyl group, alkoxycarbonylaminoalkyl of 3–12 carbon atoms, acylaminoalkyl of 3–12 carbon atoms, alkenyl of 2–7 carbon atoms, arylsulfamidoalkyl having 1–6 carbon atoms in the alkyl group, hydroxyalkylallyl of 4–9 carbon atoms, dihydroxyalkylallyl of 4–9 carbon atoms, or dioxolanylallyl; with the proviso that R¹ and R² are both not hydrogen, or a pharmaceutically acceptable salt thereof.

8. A method of treating or inhibiting rheumatoid arthritis in a mammal in need thereof, which comprises providing to said mammal an effective amount of a compound having the structure

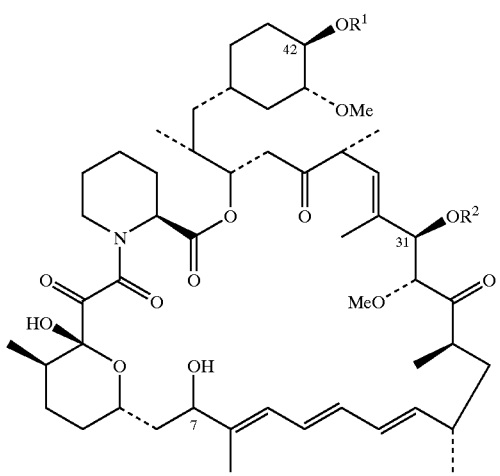

wherein

R¹ and R² are each, independently, hydrogen, thioalkyl of 1–6 carbon atoms, arylalkyl of 7–10 carbon atoms, hydroxyalkyl of 1–6 carbon atoms, dihydroxyalkyl: of 1–6 carbon atoms, alkoxyalkyl of 2–12 carbon atoms, hydroxyalkoxyalkyl of 2–12 carbon atoms, acyloxyalkyl of 3–12 carbon atoms, aminoalkyl of 1–6 carbon atoms, alkylaminoalkyl of 1–6 carbon atoms per alkyl group, dialkylaminoalkyl of 1–6 carbon atoms per alkyl group, alkoxycarbonylaminoalkyl of 3–12 carbon atoms, acylaminoalkyl of 3–12 carbon atoms, alkenyl of 2–7 carbon atoms, arylsulfamidoalkyl having 1–6 carbon atoms in the alkyl group, hydroxyalkylallyl of 4–9 carbon atoms, dihydroxyalkylallyl of 4–9 carbon atoms, or dioxolanylallyl; with the proviso that R¹ and R² are both not hydrogen, or a pharmaceutically acceptable salt thereof.

9. A method of treating or inhibiting multiple sclerosis in a mammal in need thereof, which comprises providing to said mammal an effective amount of a compound having the structure

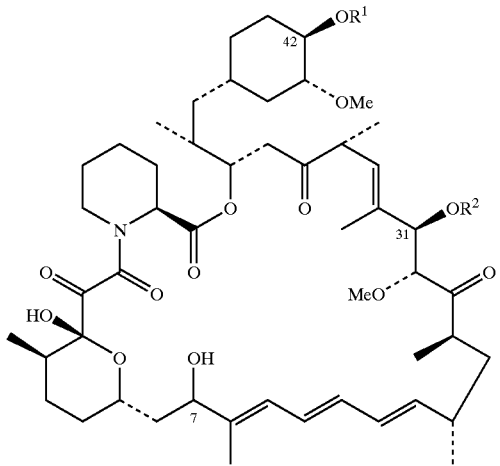

wherein

R¹ and R² are each, independently, hydrogen, thioalkyl of 1–6 carbon atoms, arylalkyl of 7–10 carbon atoms, hydroxyalkyl of 1–6 carbon atoms, dihydroxyalkyl of 1–6 carbon atoms, alkoxyalkyl of 2–12 carbon atoms, hydroxyalkoxyalkyl of 2–12 carbon atoms, acyloxyalkyl of 3–12 carbon atoms, aminoalkyl of 1–6 carbon atoms, alkylaminoalkyl of 1–6 carbon atoms per alkyl group, dialkylaminoalkyl of 1–6 carbon atoms per alkyl group, alkoxycarbonylaminoalkyl of 3–12 carbon atoms, acylaminoalkyl of 3–12 carbon atoms, alkenyl of 2–7 carbon atoms, arylsulfamidoalkyl having 1–6 carbon atoms in the alkyl group, hydroxyalkylallyl of 4–9 carbon atoms, dihydroxyalkylallyl of 4–9 carbon atoms, or dioxolanylallyl; with the proviso that R¹ and R² are both not hydrogen, or a pharmaceutically acceptable salt thereof.

10. A method of treating or inhibiting restenosis in a mammal in need thereof, which comprises providing to said mammal an effective amount of a compound having the structure

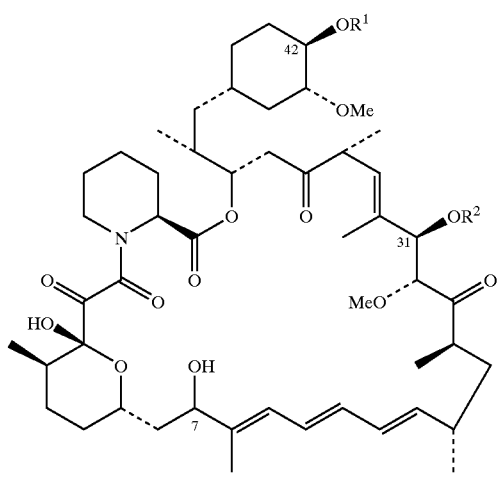

wherein

R¹ and R² are each, independently, hydrogen, thioalkyl of 1–6 carbon atoms, arylalkyl of 7–10 carbon atoms, hydroxyalkyl of 1–6 carbon atoms, dihydroxyalkyl of 1–6 carbon atoms, alkoxyalkyl of 2–12 carbon atoms, hydroxyalkoxyalkyl of 2–12 carbon atoms, acyloxyalkyl of 3–12 carbon atoms, aminoalkyl of 1–6 carbon atoms, alkylaminoalkyl of 1–6 carbon atoms per alkyl group, dialkylaminoalkyl of 1–6 carbon atoms per alkyl group, alkoxycarbonylaminoalkyl of 3–12 carbon atoms, acylaminoalkyl of 3–12 carbon atoms, alkenyl of 2–7 carbon atoms, arylsulfamidoalkyl having 1–6 carbon atoms in the alkyl group, hydroxyalkylallyl of 4–9 carbon atoms, dihydroxyalkylallyl of 4–9 carbon atoms, or dioxolanylallyl; with the proviso that R¹ and R² are both not hydrogen, or a pharmaceutically acceptable salt thereof.

11. A method of treating or inhibiting pulmonary inflammation in a mammal in need thereof, which comprises providing to said mammal an effective amount of a compound having the structure

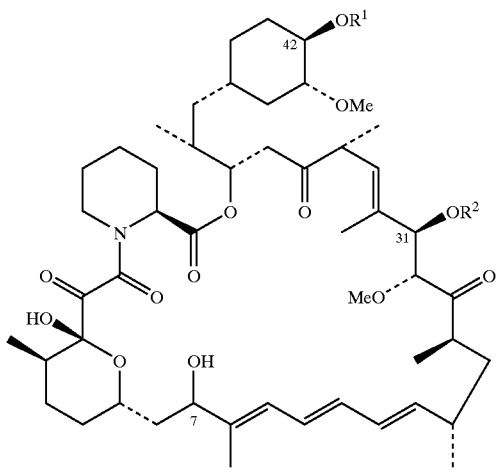

wherein

R¹ and R² are each, independently, hydrogen, thioalkyl of 1–6 carbon atoms, arylalkyl of 7–10 carbon atoms, hydroxyalkyl of 1–6 carbon atoms, dihydroxyalkyl of 1–6 carbon atoms, alkoxyalkyl of 2–12 carbon atoms, hydroxyalkoxyalkyl of 2–12 carbon atoms, acyloxyalkyl of 3–12 carbon atoms, aminoalkyl of 1–6 carbon atoms, alkylaminoalkyl of 1–6 carbon atoms per alkyl group, dialkylaminoalkyl of 1–6 carbon atoms per alkyl group, alkoxycarbonylaminoalkyl of 3–12 carbon atoms, acylaminoalkyl of 3–12 carbon atoms, alkenyl of 2–7 carbon atoms, arylsulfamidoalkyl having 1–6 carbon atoms in the alkyl group, hydroxyalkylallyl of 4–9 carbon atoms, dihydroxyalkylallyl of 4–9 carbon atoms, or dioxolanylallyl; with the proviso that R¹ and R² are both not hydrogen, or a pharmaceutically acceptable salt thereof.

12. A pharmaceutical composition which comprises a compound having the structure

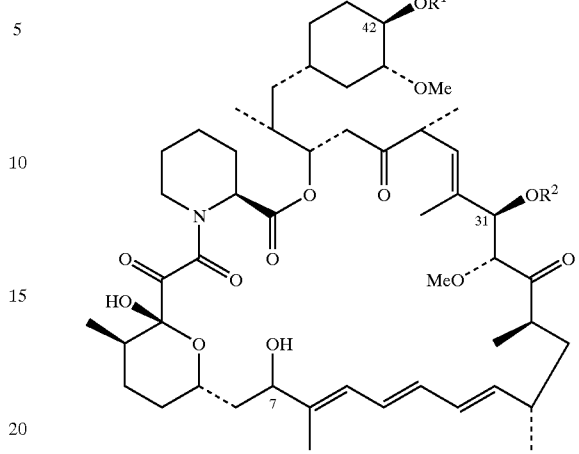

wherein R¹ and R² are each, independently, hydrogen, thioalkyl of 1–6 carbon atoms, arylalkyl of 7–10 carbon atoms, hydroxyalkyl of 1–6 carbon atoms, dihydroxyalkyl. of 1–6 carbon atoms, alkoxyalkyl of 2–12 carbon atoms, hydroxyalkoxyalkyl of 2–12 carbon atoms, acyloxyalkyl of 3–12 carbon atoms, aminoalkyl of 1–6 carbon atoms, alkylaminoalkyl of 1–6 carbon atoms per alkyl group, dialkylaminoalkyl of 1–6 carbon atoms per alkyl group, alkoxycarbonylaminoalkyl of 3–12 carbon atoms, acylaminoalkyl of 3–12 carbon atoms, alkenyl of 2–7 carbon atoms, arylsulfamidoalkyl having 1–6 carbon atoms in the alkyl group, hydroxyalkylallyl of 4–9 carbon atoms, dihydroxyaikylallyl of 4–9 carbon atoms, or dioxolanylallyl; with the proviso that R¹ and R² are both not hydrogen, or a pharmaceutically acceptable salt thereof, and a pharmaceutical carrier.

* * * * *